United States Patent [19]

Iwasa et al.

[11] Patent Number: 5,141,736
[45] Date of Patent: Aug. 25, 1992

[54] BISPECIFIC MONOCLONAL ANTIBODY, ITS PRODUCTION AND USE

[75] Inventors: Susumu Iwasa, Kyoto; Kaori Harada, Osaka; Yukio Toyoda, Hyogo, all of Japan

[73] Assignee: Takeda Chemical Industries, Ltd., Osaka, Japan

[21] Appl. No.: 457,343

[22] Filed: Dec. 27, 1989

[30] Foreign Application Priority Data

Dec. 27, 1988 [JP] Japan .................. 63-332194
Jan. 26, 1989 [JP] Japan .................. 1-018650

[51] Int. Cl.⁵ .................. A61K 39/00; A61K 35/14; C12Q 1/00; G01N 33/53
[52] U.S. Cl. .................. 530/387.3; 530/388.9; 530/388.22; 530/388.8; 530/391.7; 514/2; 435/972; 435/7.1; 435/240.26; 435/70.21; 435/172.2; 435/240.27; 424/85.8; 424/85.91
[58] Field of Search .................. 530/387; 424/85.91; 514/2; 435/240.26, 972, 7.1

[56] References Cited

U.S. PATENT DOCUMENTS

| 4,474,893 | 10/1984 | Reading | 436/547 |
| 4,713,352 | 12/1987 | Bander et al. | 436/548 |
| 4,714,681 | 12/1987 | Reading | 436/547 |
| 4,727,021 | 2/1988 | Cate et al. | 435/7 |
| 4,962,188 | 10/1990 | Frankel | 530/389 |

FOREIGN PATENT DOCUMENTS

0096076 3/1986 European Pat. Off.
8303679 10/1980 World Int. Prop. O.

OTHER PUBLICATIONS

Ghosh et al (1987) Tumor Markers & Tumor Associated Antigens, McGraw Hill, NY, pp. 239–269.
Corvalan et al (1987) Specific in vitro & in vivo drug—Cancer Immunol Immunoether 24:133–137.
Corvalan et al (1987) Increased theraputic effect—Cancer Immunol Immunoether 24:138–143.
Pirker et al et al (1985) Anti Transferrin Receptor Antibody-Cancer Res 45:751–757.
Wong et al (1987) Bispecific Monoclonal Antibody—J Immunol 139:1369–1475.
Wilstein et al (1983) Hybridhybridomas—nature 305: 537–540.
Kawac et al (1984) (Abstract & Associated Materials) Chemical modification—Chem Pharm Bull 32: 3441–3451.
Corvalan et al (1987) Construction & Charact.—Cancer Immunol Immunother 24: 127–132.
Iwasa, et al., The Physio-Chemical Biology, vol. 32, No. 5, p. 225(1988).

*Primary Examiner*—Christine M. Nucker
*Assistant Examiner*—David R. Preston
*Attorney, Agent, or Firm*—David G. Conlin; David S. Resnick

[57] ABSTRACT

The present invention discloses, a bispecific monoclonal antibody to an ansamitocin derivative and a target antigen, particularly tumor-associated antigen, which can carry an ansamitocin derivative in a stable and inactive form at other sites than the target and release the active-form ansamitocin derivative at the target site, so that an anticancer agent having excellent durability and selectivity with little adverse action can be prepared using the bispecific monoclonal antibody and ansamitocin derivatives.

24 Claims, 3 Drawing Sheets

BISPECIFIC MONOCLONAL ANTIBODY, ITS PRODUCTION AND USE

FIELD OF THE INVENTION

The present invention relates to a bispecific hybrid monoclonal antibody. More specifically, the present invention relates to a hybrid monoclonal antibody (hereinafter also referred to as hybrid MoAb) which is bispecific to an ansamitocin derivative and a target antigen, particularly tumor-associated antigen on the surface membrane of a cancer cell, and to a polydoma which produces it.

The present invention also relates to a method of cancer treatment in which the above-mentioned MoAb is used to specifically bind an ansamitocin derivative to a cancer cell, killing the cancer cell.

DESCRIPTION OF THE PRIOR ART

Ansamitocin (hereinafter also abbreviated ANS), a drug possessing potent antitumor activity, was discovered in fermentation products of an actinomycete (genus Nocardia) [E. Higashide et al.: Nature, 270, 721 (1977)]. Although an ansamitocin analog, maytansine (hereinafter also abbreviated MAY), had already been isolated as a plant-derived antitumor substance [S. M. Kupchan et al.: Journal of the American Chemical Society, 94, 1354 (1972)], much attention was given to ANS, which is derived from bacteria, since the yield of MAY is poor. Both of the drugs have an action mechanism similar to that of vinca alkaloid drugs [e.g. vincristine (hereinafter also abbreviated VCR)], inhibiting the formation of microtubules in tumor cells, thus having a cytocidal effect. The cytotoxicity of ansamitocin is 10 to 100 times as potent as that of conventional anticancer chemotherapeutic drugs (e.g. methotrexate, daunomycin). Ansamitocin and its derivatives, as a new type of antitumor agent, have been synthesized by chemical modifications and microbial conversions [A. Kawai et al.: Chemical and Pharmaceutical Bulletin, 32, 2194 (1984); H. Akimoto et al.: Chemical and Pharmaceutical Bulletin, 32, 2565 (1984); A. Kawai et al.: Chemical and Pharmaceutical Bulletin, 32, 3441 (1984)]. Through studies on the antitumor effects of these ansamitocin derivatives, in vitro and in vivo, using MAY and VCR as control drugs, as well as subacute toxicity studies including digestive tract disorder and neurotoxicity studies, several kinds of ansamitocin derivatives were found to be superior to MAY and VCR in terms of effect and safety. In particular, 9-thiomaytansine, represented by the following structural formula, showed a superior chemotherapy coefficient value (toxic amount/effective amount) to MAY and VCR.

-continued

9-Thiomaytansine

However, ANS due to its potent cytotoxicity can cause adverse effects. As a result, ANS is now in the same situation as was MAY, the development of which was stopped due to digestive tract disorder and neurotoxic action.

On the other hand, what are called 'missile therapy drugs,' namely antitumor immunocomplexes prepared by binding an antitumor antibody to a chemotherapeutic agent or a biotoxin, were developed as drugs that selectively kill tumor cells. They are characteristic of recognizing and binding to a tumor-specific antigen or tumor-associated antigen on tumor cells, and inhibiting the DNA synthesis, protein synthesis, or microtubule formation, in these tumor cells to kill them. Therefore, they are specific to tumorous organs, tissues and cells, and have little adverse action on normal cells. Some antibody-drug or antibody-toxin complexes have already been clinically applied, with some favorable results. However, the antibody activity or the pharmacological activity of the drug or toxin is often reduced due to the chemical binding reaction between the antibody and the drug or toxin protein; it is expected that more potent selective antitumor agents will be developed.

In particular, in using low molecular weight antitumor agents, there have been several problems; for example, (1) an appropriate functional group must be used for binding to an antibody, (2) chemical binding to an antibody produces a greater effect on the activity than that of a toxic protein, and normally the pharmacological activity is reduced to 1/10 to 1/100 or less, and thus (3) particular conditions must be provided under which the linker portion of the antibody-drug complex can be cleaved in tumor cells.

With this technical background, the present inventors conducted investigations to develop a new type of antibody-drug complex by binding ANS, which possesses potent cytotoxicity, to an anticancer antibody to make it tumor specific. In the preparation of such an antibody-drug complex, some problems were considered to arise as stated above. The problems posed by the conventional method utilizing chemical binding reaction include (1) remarkable reduction of the antitumor activity of the drug, as well as reduction of the binding activity of the antibody to the antigen, (2) byproduction of homopolymers formed between antibodies that are inert as selective antitumor agents or of high molecular polymers not useful in vivo due to easy metabolizability, (3) difficulty in controlling the number of drug molecules binding to the antibody, making it impossible to obtain an antibody-drug complex of constant quality, and (4) difficulty in utilizing a drug having the best therapeutic coefficient value due to the limited number of drugs usable for antibody binding to those having an appropriate functional group.

Also, recently developed hybridoma preparation techniques have permitted the preparation of new types of triomas, tetraomas and other polydomas [C. Milstein et al.: Nature, 305, 537 (1983); M. R. Suresh et al.: Proceedings of the National Academy of Science, U.S.A., 83, 7989 (1986)], thus making it possible to prepare bispecific antibodies having new functions [Japanese Unexamined Patent Publication No. 12276/1988 (Hybritech); U.S. Pat. No. 4,714,681 (University of Texas System Cancer Center)].

SUMMARY OF THE INVENTION

The present inventors conducted investigations of application and extension of the new technology described above to solve these problems. As a result, the present inventors succeeded in developing a hybrid MoAb that does not necessitate chemical binding procedures between antibody and drug molecule, which had been essential in the preparation of conventional antibody-drug complexes, and that permits preparation of an antibody-drug immunocomplex retaining the entire bioactivities of the antibody and the drug. The present inventors then prepared an anti-human-cancer protein complex using the hybrid MoAb. Accordingly, the present invention relates to a polydoma which produces a bispecific hybrid MoAb specific to both ansamitocin derivatives and target antigens, e.g. tumor-associated antigens on cancer cell membranes.

The present invention also relates to a bispecific hybrid MoAb produced by a tetraoma. This tetraoma is obtained by fusing a hybridoma, which produces an antibody against ansamitocin derivatives (hereinafter also referred to as anti-ANS antibody) and another hybridoma, which produces an antibody against target antigens, for example, human transferrin receptor (hereinafter also abbreviated hTfR), which is often expressed on cancer cell membranes. The present invention further relates to a selective anti-human-cancer protein complex obtained using this hybrid MoAb.

DESCRIPTION OF THE PREFERRED EMBODIMENTS

For the preparation of the polydoma that produces the bispecific hybrid MoAb of the present invention, an anti-ANS-antibody-producing hybridoma is used, which can, for example, be prepared by the method described below.

An ansamitocin derivative is first inoculated into an animal to elicit the production of anti-ANS antibody. In this case, the use of ANS alone as an immunogen does not normally induce the production of antibody with high titer; therefore, an ansamitocin derivative having an appropriate functional group is used as an immunogen, in conjunction with the carrier protein such as bovine serum albumin (hereinafter also abbreviated BSA) or thyroglobulin. The carrier protein can be complexed with an ansamitocin derivative via the appropriate functional group, for example, the carboxyl group of PDM-3-$C_{20}$-carboxymethyl ether or the amino group of maytansinol 3-α-aminophenylacetate or PDM-3-$C_{20}$-p-aminobenzyl ether, represented by the following formulas.

| Compound | R | Y | Q |
|---|---|---|---|
| PDM-3-$C_{20}$-carboxymethyl ether | —COCH(CH$_3$)$_2$ | —CH$_2$COOH | —OH |
| Maytansinol 3-α-aminophenylacetate | —COCH(NH$_2$)C$_6$H$_5$ | —CH$_3$ | —OH |
| PDM-3-$C_{20}$-92-aminobenzyl ether | —COCH(CH$_3$)$_2$ | —CH$_2$(C$_6$H$_4$)NH$_2$ | —OH |
| 9-Thiomaytansine | —COCHCH$_3$<br>\|<br>N(CH$_3$)COCH$_3$ | —CH$_3$ | —SH |
| MAY | —COCHCH$_3$<br>\|<br>N(CH$_3$)COCH$_3$ | —CH$_3$ | —OH |
| ANS | —COCH(CH$_3$)$_2$ | —CH$_3$ | —OH |

Note
PDM-3 represents 20-demethoxy-20-hydroxymaytansinol 3-isobutyrate.

Examples of subject animals for inoculation include rabbits, rats, mice and guinea pigs; it is especially preferable to use mice for MoAb production.

Inoculation can be achieved by an ordinary method. For example, the immunogen, in an amount of 1 to 100 μg, preferably 10 to 25 μg per inoculation, is emulsified with 0.1 ml of physiological saline and 0.1 ml of Freund's complete adjuvant, and then is inoculated, subcutaneously into the back or intraperitoneally into the abdomen, 3 to 6 times during a 2 to 3 week period.

From the group of immunized animals, mice for example, those having high antibody titer are selected. Spleens or lymph nodes are collected 3 to 5 days after the final immunization; antibody-producing cells contained therein are fused with myeloma cells. Cell fusion can be conducted in accordance with a known method. Examples of the fusogen include polyethylene glycol (hereinafter abbreviated PEG) and Sendai virus; it is preferable to use PEG. Examples of the myeloma cell line include NS-1, P3U1 and SP2/0; it is preferable to use P3U1. It is preferable that the ratio of, for example, splenocytes and myeloma cells, is 1:1 to 10:1. It is recommended that PEG with a molecular weight of 1,000 to 9,000 be added at a concentration of 10 to 80%, and that incubation be conducted at 20° to 37° C., preferably 30° to 37° C., for 3 to 10 minutes.

Various methods can be used for the screening of anti-ANS-antibody-producing hybridomas, including the ELISA method. In the ELISA method the culture supernatant of hybridomas is added to a microplate to which a (maytansinol 3-α-aminophenylacetate)-human serum albumin (hereinafter also abbreviated HSA) complex is adsorbed; next, an anti-mouse immunoglobulin antibody labeled with horseradish peroxidase (HRP) is added to the microplate, and the anti-ANS monoclonal antibody bound to the solid phase plate is then detected. Hybridomas positive for antibody activity, are selected and bred on a medium supplemented with HAT (hypoxanthine-aminopterin-thymidine). These hybridomas are immediately subjected to cloning; this cloning is normally easily achieved by, for example, limiting dilution method or other means. The antibody titer of the culture supernatants of the cloned hybridomas is determined by the above-mentioned method, to select hybridomas which stably produce an antibody with high titer. As a result, using the above-described production method, the desired monoclonal anti-ANS-antibody-producing hybridoma can be obtained.

Examples of hybridomas that are produced in accordance with the production method above and that produce anti-ANS antibody (IgG$_1$, λ chain) include mouse hybridoma AS6-44.9.

Examples of the tumor-associated antigen as the target antigen include hTfR, which is relatively highly expressed in various tumor cell lines. hTfR can be purified from human placenta tissue in accordance with a known method [P. A. Seligman et al.: Journal of Biological Chemistry, 254, 9943 (1979)]. A sample of hTfR with high purity is normally obtained by the method described below. ① Human placenta tissue is homogenized in a phosphate-buffered saline (20 mM disodium phosphate, 0.15M NaCl; hereinafter also abbreviated PBS), pH 7.5, containing 4% Triton-X-100, followed by sonication and centrifugation. ② The resulting supernatant, after being subjected to salting-out with ammonium sulfate, is applied to a column coupled with an antibody against human transferrin (hTf) and thoroughly washed with a phosphate buffer (20 mM disodium phosphate, hereinafter also abbreviated PB), pH 7.5, containing 0.5M NaCl, followed by elution of hTfR fraction with a 0.02M glycine buffer (pH 10.0) containing 0.5M NaCl and 0.5% Triton-X-100. ③ The obtained hTfR fraction is applied to a hTf-coupled column. After the column is washed with PB (pH 7.5) containing 1M NaCl, elution is conducted using a 0.5M glycine buffer (pH 10.0) containing 1M NaCl and 1% Triton-X-100 to yield a purified sample of hTfR. A single step elution and isolation is also possible using a column coupled with anti-hTfR antibody.

Animal immunization with hTfR and cell fusion of anti-hTfR-antibody-producing cells with myeloma cells can be conducted in the same manner as described for ansamitocin derivatives. Various methods can be used for the screening of anti-hTfR-antibody-producing hybridomas. Examples of such methods include the ELISA method and the cell-ELISA method. In the ELISA method the culture supernatant of the hybridomas is added to a microplate to which anti-mouse IgG antibody is adsorbed, and the purified sample of hTfR labeled with HRP is then added. The anti-hTfR monoclonal antibody bound to the solid phase plate is subsequently detected. In the cell-ELISA method, K562 cell strain which expresses a large amount of TfR on their surface membrane, is immobilized on a microplate, and the culture supernatant of hybridomas is added to the microplate, and then HRP-labeled anti-mouse IgG antibody is added.

Examples of hybridomas that are prepared in accordance with the above-mentioned production methods and produce anti-hTfR antibody (IgG1, κ chain) include mouse hybridoma 22C6.

There are several methods of preparing the polydoma of the present invention, which produces a bispecific hybrid MoAb [H. Aramoto et al.: Proteins, Nucleic Acids and Enzymes, 33, 217 (1988)]; any method can be used. Examples of such methods include ① the method in which the above-mentioned HAT-resistant, anti-ANS-antibody-producing hybridoma is acclimated step-by-step to a medium supplemented with 5-bromodeoxyuridine (hereinafter also abbreviated BrdU), followed by cloning of a thymidine kinase deficient strain and making it HAT sensitive; similarly, an HAT-resistant anti-hTfR-antibody-producing hybridoma is made resistant to 8-azaguanine (hereinafter also abbreviated AZG), followed by cloning of hypoxanthine-guanine-phosphoribosyl transferase deficient strain and making it HAT sensitive; these two strains are then fused in accordance with a conventional method to yield tetraomas, which are then cultivated on an HAT-supplemented medium for selection, followed by cloning of a tetraoma which secretes a hybrid antibody possessing a binding activity both to ansamitocin derivatives and to hTfR; and ② the method in which an anti-ANS-antibody-producing hybridoma is labeled with fluorescein isothiocyanate (hereinafter also abbreviated FITC); an anti-hTfR-antibody-producing hybridoma is labeled with tetramethyl rhodamine isothiocyanate (hereinafter also abbreviated TRITC); these two labeled hybridomas are fused in accordance with a conventional method; the obtained cell suspension is applied to a fluorescein-activated cell sorter (hereinafter also abbreviated FACS) to select and clone a tetraoma emitting both the green fluorescence of FITC and red fluorescence of TRITC. The markers for the parent strains can be reversedly used in selecting and cloning the desired tetraoma.

For cell fusion in these procedures, a fusogen such as Sendai virus or PEG, electric stimulation or other means is used. Among others, PEG is preferable. An example of the use of PEG is described below, but the present invention should not be limited to this method. PEG having a molecular weight of about 1,000 to 9,000 is used at a concentration of about 10 to 80%; treating time is about 0.5 to 30 minutes. Efficient fusion can be achieved by keeping about 35 to 55% PEG 6000 in contact with cells at 37° C. for 4 to 10 minutes; these conditions are preferable.

Polydoma selection can be achieved in the above-mentioned HAT-supplemented medium and other media; for this purposes, the drug acclimation method using 8-AZG, 6-thioguanine, 5-BrdU or other drug can be used to obtain strains resistant to the drug. Introduction of a new marker into fused cells permits the use of various selection media. Examples of such selection media include neomycin-supplemented medium and hygromycin B-supplemented medium [B. Sugden et al.: Molecular and Cellular Biology, 5, 410 (1985)]. Also available is the method in which two hybridomas labeled with different fluorescent dyes are fused, followed by sorting double-labeled hybrid hybridomas by FACS, as described above [L. Karawajew et al.: Journal of Immunological Methods, 96, 265 (1987)].

Various methods can be used for the screening of hybrid-antibody-producing polydomas. Examples of such methods include ① the above-mentioned ELISA method for the screening of anti-ANS-antibody-producing hybridomas; ② the ELISA method in which the culture supernatant of polydoma is added to a solid phase microplate to which anti-mouse immunoglobulin antibody is adsorbed, and HRP-labeled hTfR is then added to detect the anti-hTfR antibody bound to the solid phase plate; ③ the ELISA method in which the culture supernatant is added to a solid phase microplate to which a (maytansinol 3-α-aminophenylacetate)-HSA complex is adsorbed, and HRP-labeled hTfR is then added to detect the bispecific hybrid antibody; and, when using an anti-hTfR antibody (k chain) having a light chain different from that of anti-ANS antibody (λ chain), ④ the ELISA method in which the culture supernatant is added to a solid phase microplate to which a (maytansinol 3-α-aminophenylacetate)-HSA complex is adsorbed, and HRP-or biotin-labeled anti-mouse IgG-k chain specific antibody is then added to detect the bispecific antibody, and modifications of these methods; these methods can also be used in combination as appropriate.

Polydomas positive for hybrid antibody activity are subjected to cloning, which can normally be carried out easily by the limiting dilution method or other methods. The culture supernatant of the cloned polydomas is subjected to antibody titer determination by the above-mentioned method to select the polydoma that stably produces an antibody with high titer. As a result, using the methods described above, the desired hybrid monoclonal antibody-producing polydoma can be obtained.

Cultivation of the above-mentioned polydoma of the present invention can normally be carried out in a liquid medium or in the peritoneal cavity of animals (e.g. in the peritoneal cavity of mammals such as mice) by a known method. Purification of the antibody from the culture broth or ascites fluid is carried out by using a combination of known biochemical techniques. For example, the cell culture broth or ascites fluid is centrifuged; the resulting supernatant is collected and subjected to salting-out (normally using ammonium sulfate or sodium sulfate). The obtained protein precipitate is dissolved in an appropriate solution and dialyzed, and subjected to column chromatography (using, e.g., an ion exchange column, gel filtration column, Protein A column, hydroxyapatite column) to separate and purify the desired antibody. Single step separation and purification can also be conducted by the process using a column in which two different antigens have been immobilized.

The separation and purification procedures described above can yield, for example, about 1 to 5 mg of hybrid MoAb with purity not less than 80% by protein weight from 1 l of the culture supernatant. From 20 ml of the ascites fluid, 3 to 10 mg of the same antibody can be obtained.

The hybrid MoAb thus obtained is a uniform protein, and, for example, F(ab')2 fragments retaining a binding activity both to ansamitocin derivatives and to cancer-associated antigens, such as hTfR, can be obtained by proteinase treatment; these fragments can serve for the same purpose as the hybrid MoAb of the present invention.

Examples of hybrid-antibody-producing polydomas prepared in accordance with the above-mentioned production method include tetraoma ATF1-170, described in Example 2 below.

An example of the polydoma that produces the hybrid MoAb of the present invention, is the tetraoma formed between an anti-ANS MoAb-producing hybridoma and an anti-hTfR MoAb-producing hybridoma, mentioned above. It should be noted, however, that a trioma formed between a hybridoma which produces one of the MoAbs and a cell which produces the other MoAb or a hybridoma obtained by cell fusion of two cells which produce respective MoAb species after immortalization using Epstein-Barr virus or other means can serve the same purpose as the above-mentioned tetraoma, as long as they produce the hybrid MoAb of the present invention.

Moreover, in cases where these polydomas produce mouse IgG MoAb, it is possible to prepare a mouse-human chimeric antibody by obtaining DNA which encodes a variable region containing the antigen recognition site of the bispecific hybrid MoAb and ligating a gene which encodes the constant region of human IgG thereto using a gene manipulation technique [Z. Steplewski et al.: Proceedings of the National Academy of Science, USA, 85, 4852 (1988)]. This chimeric antibody is advantageously used for administration to humans because of its low antigenicity.

The bispecific antibody of the present invention, or an anti-human-cancer protein complex prepared from an ansamitocin derivative and the bispecific antibody, can be used as treatment methods in cancer therapy. Examples of such methods include ① the method in which the hybrid MoAb of the present invention is administered to the cancer-bearing patient and an ansamitocin derivative is administered after a sufficient length of time to ensure its binding to cancer tissue or cells; and ② the method in which the hybrid MoAb and an ansamitocin derivative are administered to the cancer-bearing patient simultaneously; but preferably is used ③ the method in which the hybrid MoAb and an ansamitocin derivative are reacted, and the unreacted portion of the ansamitocin derivative is separated, and then the resulting anti-human-cancer protein complex is administered to the cancer-bearing patient. In this case, any ansamitocin derivative can be used, as long as it possesses antitumor activity and is capable of reacting with the anti-ANS antibody. Examples of such ansamitocin derivarives include compounds represented by the following formula:

(I)

[wherein R represents a hydrogen atom or an acyl group derived from a carboxylic acid; Q represents a hydroxyl group (OH) or a mercapto group (SH); X represents a chlorine atom or a hydrogen atom; Y represents a hydrogen atom, a lower alkylsulfonyl group, or an alkyl group or an aralkyl group, either of which may have a substituent], and 4,5-deoxy derivatives thereof.

Examples of the acyl group derived from a carboxylic acid represented by R in the above formula (I) include acyl groups derived from carboxylic acids having a molecular weight of not greater than 300 or acyl groups having 1 to 20 carbon atoms. Examples of such acyl groups include saturated or unsaturated aliphatic acyl groups, saturated or unsaturated alicyclic acyl groups, aromatic acyl groups, and N-acyl-α-amino acid type acyl groups; they can be represented by, for example, the following formula:

—COR$^1$  (A)

[wherein R$^1$ represents a hydrogen atom, an alkyl group, an alkenyl group, a cycloalkyl group or an aryl group; these groups may have a substituent; the cyclic group above may bind to the carbonyl group via an alkylene chain]. As an example in which a substituent is contained, there is mentioned an N-acyl-α-aminoacyl group represented by the formula:

(B)

[wherein R$^2$ represents a hydrogen atom, an alkyl group, a cycloalkyl group or an aryl group; these groups may have a substituent; the cyclic group may bind to the carbon atom at the α-position via an alkylene chain; R$^3$ represents a hydrogen atom, an alkyl group, a cycloalkyl group or an aryl group; these groups may have a substituent and the cyclic group may bind to the N atom via an alkylene chain; R$^4$ represents a hydrogen atom, an alkyl group, an alkenyl group, a cycloalkyl group or an aryl group; these groups may have a substituent and the cyclic group may bind to the carbonyl group on the N atom via an alkylene chain; R$^4$ may represent an alkoxy group or a benzyloxy group].

R$^1$ in the acyl group represented by the above formula (A) is hereafter described in detail.

Examples of the alkyl group represented by R$^1$ include alkyl groups having about 1 to 18 carbon atoms (e.g. methyl, ethyl, propyl, isopropyl, butyl, isobutyl, sec-butyl, tert-butyl, pentyl, isopentyl, 1-methylpropyl, hexyl, heptyl, 3-heptyl, octyl, nonyl, decyl, undecyl, dodecyl, tridecyl, pentadecyl and heptadecyl groups). Among others, a lower alkyl group having about 1 to 6 carbon atoms is preferable.

Examples of the alkenyl group represented by R$^1$ include alkenyl groups having about 2 to 10 carbon atoms (e.g. vinyl, allyl, 1-methyl-vinyl, 2-methyl-vinyl, 1-octenyl and 1-decenyl groups). Among others, a lower alkenyl group having about 2 to 4 carbon atoms is preferable.

Examples of the cycloalkyl group represented by R$^1$ include cycloalkyl groups having about 3 to 10 carbon atoms (e.g. cyclopropyl, cyclobutyl, cyclopentyl, cyclohexyl, cycloheptyl, cyclooctyl, nonybornyl and adamantyl groups).

Examples of the aryl group represented by R$^1$ include a phenyl group and a naphthyl group. A phenyl group is preferable.

The alkyl group, the alkenyl group, the cycloalkyl group and the aryl group as R$^1$ may have a substituent. Examples of the substituent include lower alkoxy groups having 1 to 4 carbon atoms (e.g. methoxy, ethoxy, propoxy, isopropoxy, butoxy, isobutoxy, sec-butoxy and tert-butoxy groups), lower alkanoyl groups having 2 to 4 carbon atoms (e.g. acetyl, propionyl, butyryl and isobutyryl groups), lower alkanoyloxy groups having 2 to 4 carbon atoms (e.g. acetyloxy, propionyloxy, butyryloxy and isobutyryloxy groups), lower alkoxycarbonyl groups having 2 to 4 carbon atoms (e.g. methoxycarbonyl, ethoxycarbonyl, propoxycarbonyl and isopropoxycarbonyl groups), halogen atoms (e.g. chlorine, fluorine, bromine and iodine atoms), hydroxyl groups, nitro groups, cyano groups, trifluoromethyl groups, amino groups, mono-lower ($C_{1-4}$) alkylamino groups (e.g. methylamino group), dilower ($C_{1-4}$) alkylamino groups (e.g. dimethylamino, diethylamino, dipropylamino, diisopropylamino and dibutylamino groups), lower alkylthio groups having 1 to 4 carbon atoms (e.g. methylthio, ethylthio, propylthio, isopropylthio, butylthio, isobutylthio, sec-butylthio and tert-butylthio groups), lower ($C_{1-4}$) alkylsulfinyl groups, lower ($C_{1-4}$) alkanesulfonyl groups, oxo groups, thioxo groups and lower alkanoylamino groups having 1 to 4 carbon atoms (e.g. formylamino, acetylamino, propionylamino, butyrylamino and isobutyrylamino groups). When R$^1$ above is a cyclic group (cycloalkyl or aryl group), examples of the substituents also include lower alkyl groups having 1 to 4 carbon atoms (e.g. methyl, ethyl, propyl, isopropyl, butyl, isobutyl, sec-butyl and tert-butyl groups). The groups may be substituted by 1 to 3 members of the same or different species of the substituents.

The cyclic group (cycloalkyl or aryl group which may have a substituent) represented by R$^1$ may bind to the carbonyl group in the formula —COR$^1$ via an alkylene chain. Examples of the alkylene chain include straight or branched lower alkylene chains having about 1 to 4 carbon atoms (e.g. methylene, ethylene, methylmethylene (ethylidene), propylene, butylene, 1-, 2- or 3-methylpropylene, 1- or 2-ethylethylene, propylmethylene, 1,1- or 1,2-dimethylethylene, isopropylmethylene). The alkylene chain may have a substituent which is mentioned above. Accordingly, when the cyclic group and the alkylene chain bind together, R$^1$ represents a cycloalkylalkyl group or an aralkyl group which may have a substituent.

Examples of the alkyl group represented by R$^1$ having 1 to 18 carbon atoms and a substituent include methoxymethyl, butoxymethyl, methylthiomethyl, methylthioethyl, ethylthioethyl, isopropylthioethyl, butylthioethyl, isobutylthioethyl, acetyloxymethyl, acetyloxyethyl, ethoxycarbonylmethyl, butoxycarbonylethyl, fluoromethyl, chloromethyl, chloroethyl, 3-chloropropyl, 4-chlorobutyl, trifluoromethyl, bromomethyl, 4-bromobutyl, 5-bromopentyl, iodomethyl, 2-iodoethyl, cyanomethyl, methylsulfinylethyl and methylsulfonylmethyl.

Examples of the alkenyl group represented by R$^1$ having 2 to 10 carbon atoms and a substituent include 2-ethoxycarbonylvinyl.

Examples of the cycloalkyl group represented by R$^1$ having 3 to 10 carbon atoms and a substituent include 2,2-dimethylcyclopropyl, 4-isobutylcyclohexyl, 2-bromocyclopropyl, 2-chlorocyclobutyl, 4-chlorocyclohexyl, 2,2-difluorocyclobutyl, 3-methoxycyclohexyl, 4-acetylcyclohexyl, 2-cyanocyclobutyl, 4-cyanocyclohexyl and 4-dimethylaminocyclohexyl.

Examples of the aryl group represented by $R^1$ having a substituent include 2-, 3- or 4-methylphenyl, 4-tert-butylphenyl, 2-, 3- or 4-chlorophenyl, 2-, 3- or 4-bromophenyl, 2-, 3- or 4-iodophenyl, 2-, 3- or 4-fluorophenyl, 2- or 4-methoxyphenyl, 4-butoxyphenyl, 4-methoxycarbonylphenyl, 3-acetylphenyl, 2-, 3- or 4-nitrophenyl, 3- or 4-cyanophenyl, 4-dimethylaminophenyl, 4-diethylaminophenyl, 4-acetoxyphenyl, 4-butyryloxyphenyl, 3,4-dimethoxyphenyl, 3,4,5-trimethoxyphenyl, 3,4-methylenedioxyphenyl, 3-trifluoromethylphenyl, 4-methylthiophenyl, 4-methylsulfonylphenyl and 4-acetamidophenyl.

When the cyclic group represented by $R^1$ described above [e.g. cycloalkyl and aryl (particularly phenyl) groups] binds to the carbonyl carbon of the acyl group in the formula (A) via an alkylene chain, $R^1$ essentially represents a group comprising one of these cyclic groups and an alkylene chain bound thereto, for example, a cycloalkylalkyl group or an aralkyl group. Examples of the cycloalkylalkyl group include adamantylmethyl, cyclohexylmethyl, 3-cyclohexylpropyl, 2-cyclopentenylmethyl and 2-cyclopentylethyl. Examples of the aralkyl group include 4-bromobenzyl, 2-, 3- or 4-cyclobenzyl, 2,5- or 3,4-dimethoxybenzyl, 4-ethoxybenzyl, 4-fluorobenzyl, 3- or 4-methoxybenzyl, 4-methoxyphenylethyl, 1- or 2-naphthylmethyl, 2-, 3- or 4-nitrobenzyl, 3-nitrophenethyl, benzyl, 2-, 3- or 4-phenylpropyl, 2-, 3- or 4-methylbenzyl, 3,4,5-trimethoxybenzyl and α-methylphenethyl.

The N-acyl-α-aminoacyl group represented by the above formula (B) is described below.

The alkyl, alkenyl, cycloalkyl and aryl groups defined for $R^2$, $R^3$ or $R^4$ are exemplified by the same groups as those mentioned as examples for $R^1$ above. These groups may have a substituent. The substituent is exemplified by the same groups as those mentioned as examples for the substituent for $R^1$ above. The cyclic group for $R^2$, $R^3$ or $R^4$ (i.e. cycloalkyl or aryl group) may bind to the carbon atom at the α-position, the N atom or the carbonyl group attaching to the N atom in the formula (B) via an alkylene chain. The alkylene chain is exemplified by the same alkylene chains as those described referring to $R^1$ above.

Examples of the alkoxy group represented by $R^4$ include lower alkoxy groups having about 1 to 4 carbon atoms (e.g. methoxy, ethoxy, propoxy, isopropoxy, butoxy, isobutoxy, sec-butoxy and tert-butoxy groups).

Representative examples of the N-acyl-α-aminoacyl group represented by the formula (B) include N-acetyl-N-methyl-glycyl, N-benzoyl-N-methylglycyl, N-(4-chlorobenzoyl)-N-methyl-glycyl, N-acetyl-N-methyl-alanyl, N-acetyl-N-benzyl-alanyl, N-acetyl-N-methyl-leucyl, N-isobutyryl-N-methylalanyl, N-isovaleryl-N-methyl-alanyl, N-propionyl-N-methyl-alanyl, N-acetyl-N-methyl-phenylalanyl, 2-(N-acetyl-N-methyl)amino-3-methoxycarbonylpropionyl, 2-(N-acetyl-N-methyl)amino-3-methylmercaptopropionyl, 2-(N-acetyl-N-methyl)amino-3-ethylmercaptopropionyl, N-acetyl-N-methylisoleucyl, N-acetyl-N-methyl-leucyl, N-acetyl-N-methyl-methionyl, N-acetyl-N-methyl-phenylalanyl, N-acetyl-N-methyl-4'-acetoxy-tyrosinyl, N-benzyl-N-methyl-valyl, N-acetyl-N-methyl-phenylglycyl, N-acetyl-N-methyl-3-cyanoalanyl and N-acetyl-N-methyl-(4'-dimethylamino)-phenylalanyl.

Examples of the lower alkylsulfonyl group represented by Y in the above formula (I) include alkylsulfonyl groups having about 1 to 4 carbon atoms (e.g. methanesulfonyl, ethanesulfonyl, 2-propanesulfonyl, 2-butanesulfonyl).

Examples of the alkyl group represented by Y include lower alkyl groups having about 1 to 8 carbon atoms (e.g. methyl, ethyl, propyl, isopropyl, butyl, sec-butyl, pentyl, isopentyl, hexyl, heptyl, octyl). Examples of the aralkyl group include phenyl-lower ($C_{1-4}$) alkyl groups (e.g. benzyl, 2-phenethyl, 3-phenylpropyl). The alkyl group and the aralkyl group for Y may have a substituent. Examples of the substituent include hydroxyl groups, amino groups, lower ($C_{1-4}$) acylamino groups, lower ($C_{1-4}$) alkyloxy groups, benzyloxy groups, oxo groups, halogen (chlorine, bromine, iodine) atoms, trifluoromethyl groups, lower ($C_{2-5}$) alkoxycarbonyl groups, carboxyl groups, methylenedioxy groups and lower ($C_{1-4}$) alkylthio groups.

Examples of the corresponding 4,5-deoxy derivatives include compounds represented by the formula:

[wherein the symbols are as defined above].

The above-mentioned ansamitocin derivatives can be synthesized by, for example, the methods described in Kupchan et al., the Journal of the American Chemical Society, 97, 5294 (1975), Higashide et al., Nature, 270, 271 (1977), U.S. Pat. Nos. 4,137,230, 4,151,042, 4,162,940, 4,228,239, 4,229,533, 4,248,870, 4,256,746, 4,260,608, 4,263,294, 4,264,596, 4,265,814, 4,294,757, 4,307,016, 4,308,268, 4,308,269, 4,309,428, 4,317,821, 4,322,348, 4,331,598, 4,356,265, 4,362,663, 4,371,533 and 4,424,219 or similar methods thereto.

The target antigen in the present invention includes various antigens; representative examples include cancer cell membrane surface antigens such as tumor-associated antigens, immunocompetent cell surface receptors and virus infected cell surface antigens. Among these antigens, hTfR is often used as the tumor-associated antigen, but carcinoembryonic antigen (what is called CEA), α-fetoprotein and several cancer-associated sugar chain antigens including CA19-9 [S. Hakomori: Cancer Research, 45, 2405 (1985)], B-cell lymphoma membrane immunoglobulin idiotypes [R. A. Miller et al.: New England Journal of Medicine, 306, 517 (1982)], T-cell lymphoma receptor idiotypes [L. L. Lanier et al.: Journal of Immunology, 137, 2286 (1986)] and glycoprotein which is expressed specifically on renal cell carcinoma are also usable.

As mentioned above, the hybrid MoAb of the present invention is capable of very specific binding to the target antigen and efficiently killing cancer cells by the cytotoxic action of the ansamitocin derivative bound thereto, thus permitting selective and effective cancer treatment.

The hybrid MoAb of the present invention neutralizes the cytotoxicity of an ansamitocin derivative by binding with the ansamitocin derivative, and releases the ansamitocin derivative at the target site to produce the cytotoxic effects. Thus, the hybrid MoAb of the present invention can carry an ansamitocin derivative in a stable and inactive form at other sites than the target site and release the active-form ansamitocin derivative at the target site. As a result, the present invention provides an anticancer agent having excellent durability and selectivity, with very little adverse action.

The present invention is hereinafter described in more detail by means of reference and working examples; these examples are not to be construed as limitations on the scope of the invention.

| Deposition of animal cells at deposition institutions | | |
|---|---|---|
| Animal cell line | IFO (IFO No.) | FRI (FERM No.) |
| Mouse hybridoma AS6-44.9 | 50181 | BP-2233 |
| Mouse-mouse hybridoma 22C6 | 50172 | BP-2054 |
| Mouse hybridoma ATF1-170 | 50182 | BP-2234 |
| Mouse hybridoma RCS-1 | 50184 | BP-2333 |
| Mouse hybridoma RCAS1-488 | 50218 | BP-2687 |

IFO Institute for Fermentation, Osaka
FRI Fermentation Research Institute, Agency of Industrial Science and Technology, Ministry of International Trade and Industry Brief Description of The Drawings

REFERENCE EXAMPLE 1

(ELISA for anti-ANS antibody assay)

① Preparation of solid phase antigen

Maytansinol 3-α-aminophenylacetate maleimidated with N-(γ-maleimido-butyryloxy)-succinimide was added to HSA which had been subjected to modification reduction with N-succinimidylpyridyl dithiopropionate to yield a (maytansinol 3-α-aminophenylacetate)-HSA complex by thiol exchange reaction. To a 96-well microplate was added a 50 μg/ml solution of this protein complex at 100 μl/well to yield a solid phase antigen.

② Assay method

To the above antigen-sensitized plate was added 100 μl of the subject culture supernatant of hybridoma, followed by reaction at room temperature for 2 hours. After thorough washing of the plate with a 20 mM phosphate buffered saline solution containing 0.05% Tween 20 (pH 7.3, hereinafter abbreviated PBS-Tw), an HRP-labeled anti-mouse IgG rabbit antibody was added, and reaction was carried out at room temperature for 2 hours.

After the plate was washed again, a 0.1M citrate buffer solution containing ortho-phenylenediamine and $H_2O_2$ as enzyme substrates was added to each well, and enzyme reaction was carried out at room temperature. After termination of the reaction by the addition of 1N sulfuric acid, the amount of coloring pigment was determined at a wavelength of 492 nm using a Multiscan (produced by Flow Co.).

REFERENCE EXAMPLE 2

(Preparation of anti-hTfR-antibody-producing hybridoma)

① Purification of hTfR 1.5 kg of human placenta tissue was cut into small pieces and blended in PBS (pH 7.5), followed by centrifugation. The resulting sediment was homogenized in PBS containing 4% Triton X-100. This homogenate was ultrasonicated and then centrifuged. To the resulting supernatant was added ammonium sulfate at about 32 g per 100 ml supernatant. After salting-out, this mixture was applied to a column coupled with anti-hTf antibody, followed by thorough washing with PB (pH 7.5) containing 0.5M NaCl. The hTfR fraction eluted with a 0.02M glycine buffer solution (pH 10.0) containing 0.5M NaCl and 0.5% Triton X-100 was applied to an hTf-coupled column. After the column was washed with PB containing 1M NaCl, elution was conducted using a 0.05M glycine buffer solution (pH 10.0) containing 1M NaCl and 1% Triton X-100 to yield about 1.5 mg of a purified sample of hTfR.

② Immunization

To a 200 μg/ml solution of the above purified sample of hTfR in physiological saline was added an equal volume of Freund's complete adjuvant, followed by thorough emulsification. The resulting emulsion was then administered intraperitoneally and subcutaneously at the back to BALB/c mice (female, n=10, 20 μg/ml/mouse). Additional immunization was conducted at intervals of 3 weeks. The animal that showed the maximum serum antibody titer 2 weeks after 4 additional immunizations was intravenously given the same hTfR antigen solution as specified above (30 μg/0.1 ml physiological saline/mouse).

③ Cell fusion 3 days after the final immunization, the spleen was excised and a splenocyte suspension was prepared by a conventional method (approximately $10^8$ cells). To this suspension was added $2 \times 10^7$ mouse myeloma cells (P3U1), followed by cell fusion using PEG6000 in accordance with the method of Köhler and Milstein [Nature, 256, 495 (1975)].

After completion of cell fusion, the cell mixture was suspended in HAT medium containing hypoxanthine, aminopterin and thymidine, followed by cultivation for 10 days. After selection of parent cells, cultivation was continued using HT medium which had the same composition as that of HAT medium but not including aminopterin.

④ Selection and cloning of hypridomas

A commercially available anti-mouse IgG rabbit antibody solution (20 μg/ml) was dispensed to a 96-well microplate at 100 μl per well. After this microplate was allowed to stand at 4° C. overnight, PBS (pH 7.3) containing 2% BSA was added to prepare a sensitized plate. The purified sample of hTfR obtained in ①, after being labeled with HRP in accordance with a conventional method, was used for ELISA [T. Kitagawa: *Yuki Gosei Kagaku*, 42, 283 (1984)]. Accordingly, the culture supernatant of hybridomas was added to the above second antibody-sensitized plate, and reaction was carried out at room temperature for 2 hours. After the plate was washed with PBS, HRP-labeled hTfR was added, followed by reaction at room temperature for 2 hours. Enzyme reaction was then carried out by the method described in Reference Example 1-②, to determine the antibody titer.

The hybridoma showing especially high binding activity was subjected to cloning by limiting dilution method to yield anti-hTfR-antibody-producing hybridoma 22C6. The present antibody was identified as the $IgG_1$ ($\kappa$ chain) subclass, exhibiting high affinity to human tumor cell strain K562.

REFERENCE EXAMPLE 3

(Mixed hemagglutination assay, MHA)

Among the subject cells, adherent cells (500 cells/well) were dispensed to a 60-well microplate (Nunc) and cultivated for 24 to 48 hours, while non-adherent cells were suspended in a medium with no serum, dispensed to wells (500 cells/well) and centrifuged at 400×g for 5 minutes for adhesion of the cells to the plate.

The indicator blood cells were prepared as follows: Sheep red blood cells were washed with PBS 3 times and suspended in PBS to prepare a 2% suspension. The suspension was reacted with the same volume of mouse antisheep red blood cell antibody (Ortho) which was previously 2.5-fold diluted on maximum agglutination titer with PBS, at 37° C. for 30 minutes. The blood cells were washed with PBS 3 times and suspended again in PBS in a concentration of 2%. The suspension was reacted with the same volume of rabbit anti-mouse IgG antibody (Cappel) which was previously 25-fold diluted with PBS, at 37° C. for 30 minutes. The blood cells were then washed with PBS 3 times and preserved as a 2% suspension.

The cell-adhering plate was washed with 0.1M $MgCl_2$-0.03M $CaCl_2$-0.1% glucose-containing Veronal buffered saline (pH 7.4, hereinafter abbreviated VBS) which further contained 5% FCS. A culture supernatant or ascites fluid was dispensed to each well of the plate and allowed to stand at room temperature for 1 hour. The plate was washed with VBS, and then the indicator blood cell suspension which was diluted with 5% FCS-VBS to 0.2% was dispensed to each well and allowed to stand at room temperature for 40 minutes. The plate was washed with VBS to remove unreacted blood cells and then observed by a microscope. In the control test, in which no antibody was added, a rosette was formed in not greater than 1% of the cells. A "positive" test was defined as a rosette formed by not less than 25% of the subjected cells.

REFERENCE EXAMPLE 4

(Preparation of anti-human renal cell carinoma monoclonal antibody-producing hybridoma)

① Transplantation of human renal cancer cell and immunization by sera

A nu/nu-BALB/c mouse was subcutanously given a tumor tissue graft (2 mm square) from a patient with renal cancer to obtain a well-established renal cancer cell AM-RC-3, which was then subcutanously transplanted to a syngeneic nu/nu-BALB/c mouse. After 3 to 4 weeks, sera were collected. A syngeneic BALB/c mouse was intraperitoneally given 0.5 ml of the sera with the same volume of Freund's complete adjuvant 6 times at 7- to 10-day intervals, and then the mouse was intraperitoneally given 1.0 ml of the sera (final immunization). After the final immunization the antibody titer was determined by the MHA method described in Reference Example 3.

② Preparation of Hybridoma

Spleen cells of the immunized mouse which exhibited a high antibody titer were fused with mouse myeloma cells, NS-1, according to a conventional method (treatment with PEG6000 at 37° C. for 1 to 10 minutes), and hybridomas were selected using HAT medium ($1\times10^{-4}$M hypoxanthine, $4\times10^{-7}$M aminopterin and $1.6\times10^{-5}$M thymidine). Growing hybridoma groups were screened by the MHA method described in Reference Example 3. The group exhibiting a high antibody titer was further cloned to obtain antihuman renal cancer carinoma MoAb-producing mouse hybridoma RCS-1. RCS-1 antibody produced by mouse hybridoma RCS-1 was identified as the $IgG_1$ subclass.

③ Production of Mouse MoAb

An MCH (AF)-nu mouse was intraperitoneally given $5\times10^6$ mouse hybridoma RCS-1 cells. After about 4 weeks, 5 to 10 ml of ascites fluid was collected. The collected ascites fluid was subjected to salting-out with ammonium sulfate and then purification by a column of DEAE-cellulose. About 200 mg of the purified mouse anti-human renal cell carcinoma MoAb RCS-1 was obtained from 50 ml of ascites fluid.

④ Characteristics of Mouse Anti-Human Renal Cell Carcinoma MoAb

The reactivity of mouse MoAb RCS-1 with various human tumor cells and normal renal tissues was determined using the MHA method described in Reference Example 3. The results are shown in the following Table.

The table clearly shows that the antibody has strong reactivity to all kinds of the subjected renal cancer cells while it is not reacted with normal renal tissues. Further, the antibody is reactive with a part of lung cancer cells, bladder cancer cells and T-cell leukemia cells.

TABLE (Reactivity of mouse monoclonal antibody RCS-1[1])

Positive cell groups:
Renal cancer (AM-RC-3, AM-RC-6, AM-RC-7, SK-RC-1, SK-RC-9, SK-RC-18)
Bladder cancer (T-24)
Lung cancer (Luci-10, Calu-6, PC-10)
T-cell leukemia (HUT-78)

Negative cell groups:
Bladder cancer (KK-47, MGH-U-1)
Prostate cancer (DU-145)
Stomach cancer (NUGC-2, NUGC-3, NUGC-4, MKN-28, KATO-III, MRK-1)
Intestine cancer (SW-403, SW-620, SW-1116, SW-1222, CaOV-4, HT-29)
Uterocervical cancer (ME-180)
Melanoma (SK-MEL-33, SK-MEL-37)
Breast cancer (MCF-7)
Glioma (MG-178)
Lung cancer (ADLC-DA, SBC-3, SCLC-SA, Luci-6, CADO-LC3, OKADA, QG-56)
T-cell leukemia (CCRF-CEM, HPB-ALL, HSB-2, TABLE-continued (Reactivity of mouse monoclonal antibody RCS-1[1])

HUT-102, RPMI-8402, P12/Ichikawa, MT-1, MT-2)
B-cell leukemia (Raji, Daudi, BALL-1, RPMI-1788, Ly-16)
Null cell leukemia (NALL-1, NALM-6, NALM-18,
KOPN-K, P30/Ohkubo)
Myelocytic leukemia (HL-60)
Negative tissue groups
Normal kidney (5 kinds)

[1]Determined by the MHA method of Reference Example 3

EXAMPLE 1

(Preparation of anti-ANS-antibody-producing hybridoma and immunization)

PDM-3-$C_{20}$-carboxymethyl ether was converted to an active ester by N-hydroxysuccinimide and dicyclohexylcarbodiimide and then bound to the carrier protein BSA to yield an immunogen.

To a 200 µg/ml physiological saline solution of the (PDM-3-$C_{20}$-carboxymethyl ether)-BSA complex thus obtained an equal volume of Freund's complete adjuvant was added, followed by thorough emulsification. The resulting emulsion was administered intraperitoneally and subcutaneously at the back to BALB/c mice (female, 20 µg/0.2 ml/mouse). Additional immunization was conducted at intervals of 2 to 3 weeks. The animal showing the maximum serum antibody titer 10 days after 3 additional immunizations was intravenously given a solution of (PDM-3-$C_{20}$-carboxymethyl ether)-BSA complex (50 µg/0.1 ml physiological saline/mouse).

② Cell fusion

Cell fusion was conducted in accordance with the method described in Reference Example 2-③.

③ Selection and Cloning of Hybridomas

Hybridomas were screened by the ELISA method of Reference Example 1 using a microplate coupled with (maytansinol 3-α-aminophenylacetate)-HSA, followed by the same procedure as in Reference Example 2-④ to yield anti-ANS MoAb-producing hybridomas. From these hybridomas was selected a mouse hybridoma AS6-44.9, which shows strong binding activity to 9-thiomaytansine, MAY and ANS as well as to the immunogen PDM-3-$C_{20}$-carboxymethyl ether. Immunoglobulin class, subclass and light chain type of the present antibody were determined to be IgG$_1$-λ chain by the Ouchterlony and ELISA methods. The antibody was found to be capable of neutralizing the cytotoxicity of ANS.

Figure 1:
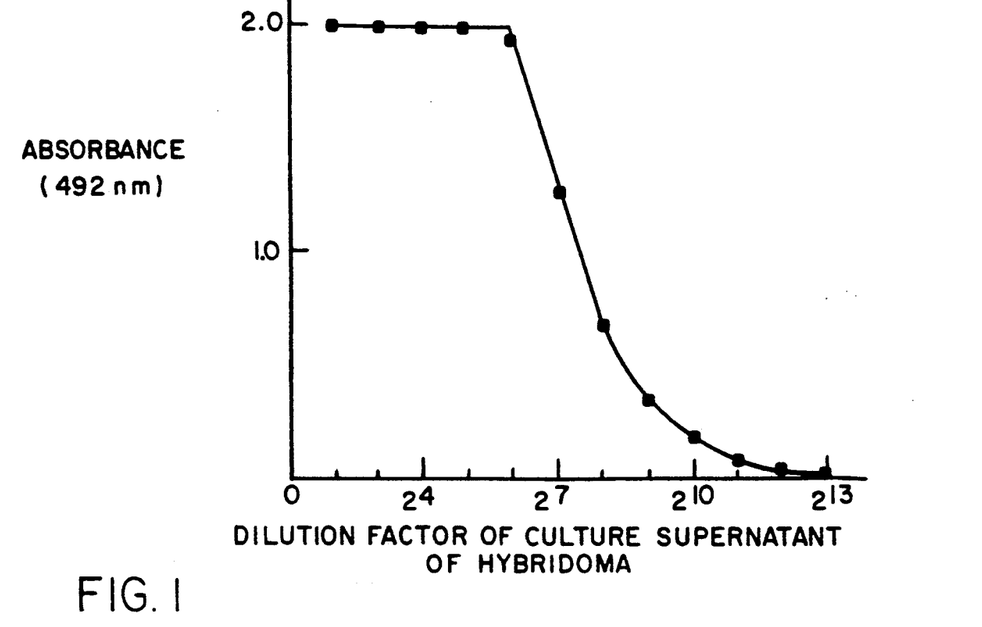
FIG. 1 shows the antibody dilution curve obtained by subjecting the anti-ANS antibody AS6-44.9 prepared in Example 1 to the ELISA method described in Reference Example 1.
Figure 2:
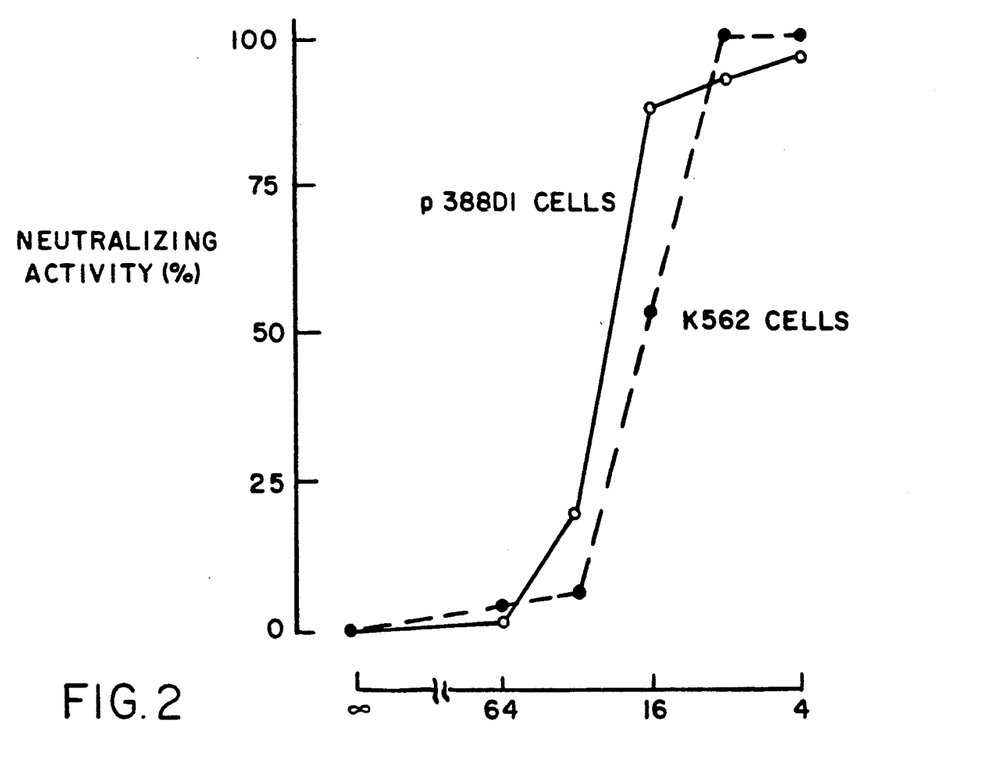
FIG. 2 shows the neutralizing activity curve of the same AS6-44.9 antibody against ANS (1 ng/ml).

FIG. 1 shows the antibody dilution curve using ELISA for the culture supernatant of hybridoma AS6-44.9. FIG. 2 shows the neutralization activity curves for the cytotoxicity of ANS (target cell lines: mouse leukemia cell line P388D1 and human leukemia cell line K562).

EXAMPLE 2

(Production of anti-ANS-anti-hTfR bispecific hybrid monoclonal antibody)

① Cell fusion

The anti-ANS-antibody-producing hybridoma AS6-44.9, obtained in Example 1, and the anti-hTfR-antibody-producing hybridoma 22C6, obtained in Reference Example 2, were each incubated at 37° C. for 30 minutes for fluorescent staining in an Iskove-Ham F12 mixed medium containing either 0.5 µg/ml FITC for hybridoma AS6-44.9 or 1.5 µg/ml TRITC for hybridoma 22C6. After addition of an LSM solution (commercially available from Wako Pure Chemical Industries, Ltd.) and removal of dead cells, these two hybridomas were mixed together at a ratio of 1:1 and subjected to cell fusion using PEG6000.

After incubation for 2 hours at 37° C., the cells were applied to FACS, whereby 25,000 fluorescein-rhodamine double stained cells were sorted. These double-stained cells (10 cells/well) were sown to and cultivated in a 96-well microplate seeded with $5 \times 10^5$ cells/well mouse thymocytes as feeder cells, with 10 double-stained cells per well.

② Selection and Cloning of Hybrid Hybridomas

The culture supernatants in the wells in which cell proliferation occurred 1 to 2 weeks after cell fusion were subjected to the following ELISA procedure for bispecific antibody assay to determine their antibody titer. To the (maytansinol 3-α-aminophenylacetate)-HSA sensitized plate prepared in Reference Example 1-① the subject culture supernatant of hybrid hybridomas was added, followed by reaction at room temperature for 2 hours. After the plate was washed with PBS-Tw, a biotin-labeled anti-mouse IgG-κ chain-specific antibody was added, followed by reaction at room temperature for 2 hours. Then, HRP-labeled avidin was added and the plate was washed. The activity of the enzyme bound to the solid phase was determined by the method described in Reference Example 1-②.

Figure 3:
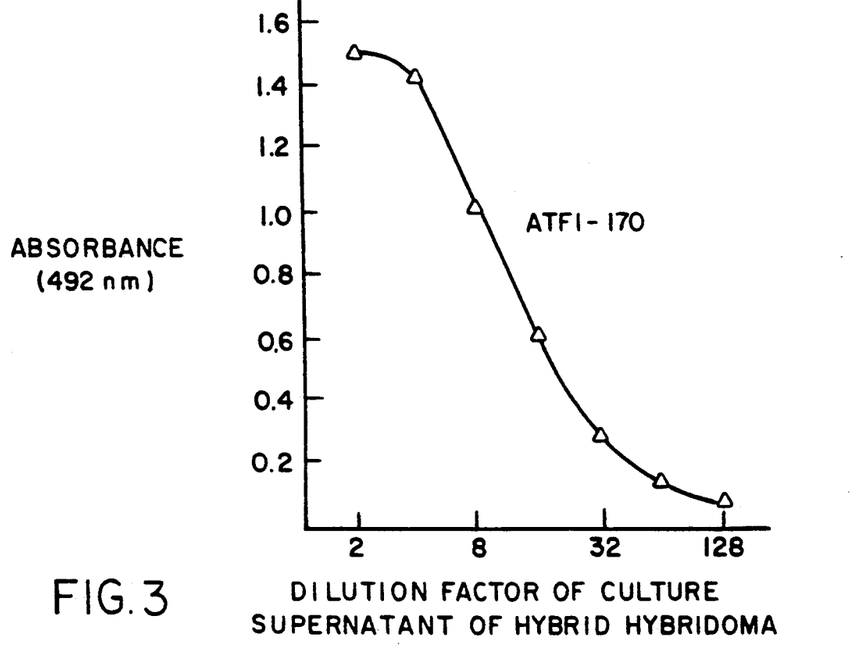
FIG. 3 shows the bispecific antibody activity of the hybrid antibody ATF1-170 prepared in Example 2.

Wells showing a high level of hybrid antibody activity were subjected to cloning by the limiting dilution method, whereby the desired bispecific-antibody-producing tetraoma ATF1-170 was obtained. FIG. 3 shows the antibody dilution curve of the culture supernatant of ATF1-170.

③ Purification of Hybrid Antibody $5 \times 10^6$ tetraoma cells per mouse were intraperitoneally inoculated to six BALB/c mice which had been intraperitoneally given 0.5 ml mineral oil. Ascites fluid retention began to occur 14 to 18 days later. The ascites fluid was collected and subjected to salting-out with 45 to 50% saturated ammonium sulfate to yield an IgG fraction. After dialysis against 20 mM PBS (pH 7.5), this fraction was applied to a column of Cellulofine coupled with PDM-3-$C_{20}$-$p$-aminobenzyl ether and eluted with 0.2M glycine-HCl buffer solution (pH 2.9). The acidically eluted fraction was dialyzed against PBS and then subjected to high performance liquid chromatography using a column of hydroxyapatite to yield the anti-ANS-anti-hTfR bispecific hybrid antibody of the present invention.

About 7.3 mg of the bispecific antibody was obtained from 20 ml of ascites fluid.

EXAMPLE 3

(Isolation of anti-ANS-anti-hTfR-bispecific hybrid monoclonal antibody)

Tetraoma ATF1-170 was inoculated to BALB/c mice by the method described in Example 2-③ to obtain ascites fluid. The collected ascites fluid was subjected to salting-out with 45 to 50% saturated ammonium sulfate and then purification by a column of Protein A to yield an IgG fraction. This acidically eluted fraction was dialyzed against a 10 mM potassium phosphate buffer solution (pH 6.2) and applied to a column of hydroxyapatite equilibrated with the same buffer solution. Elution was conducted using a density gradient of from 10 mM to 300 mM of potassium phosphate buffer solution (pH 6.2) to separate various immunoglobulin species. The results are shown in FIG. 4.

Figure 4:
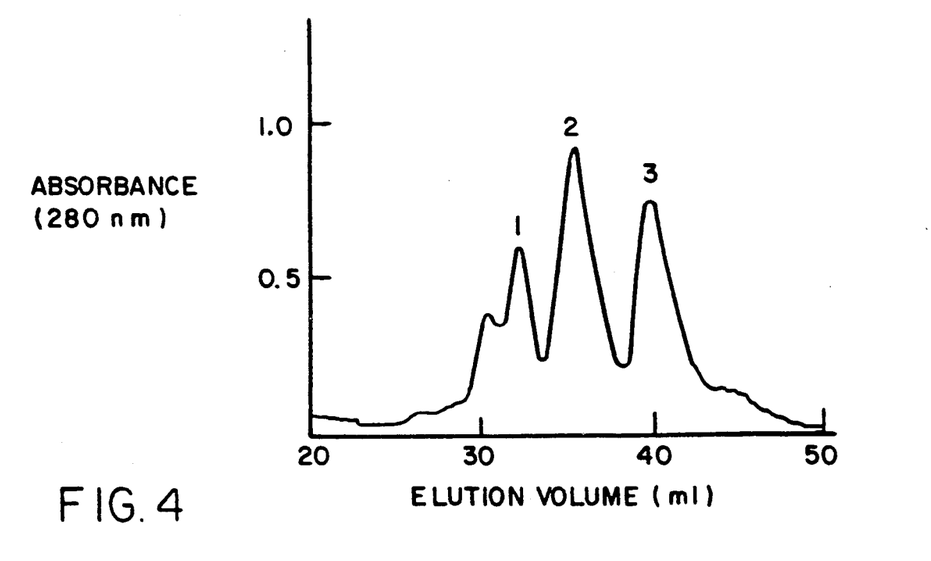
FIG. 4 shows the hydroxyapatite column elution curve of the immunoglobulin species produced by the tetraoma ATF1-170 prepared in Example 3, on the basis of absorbance at 280 nm.
Figure 5:
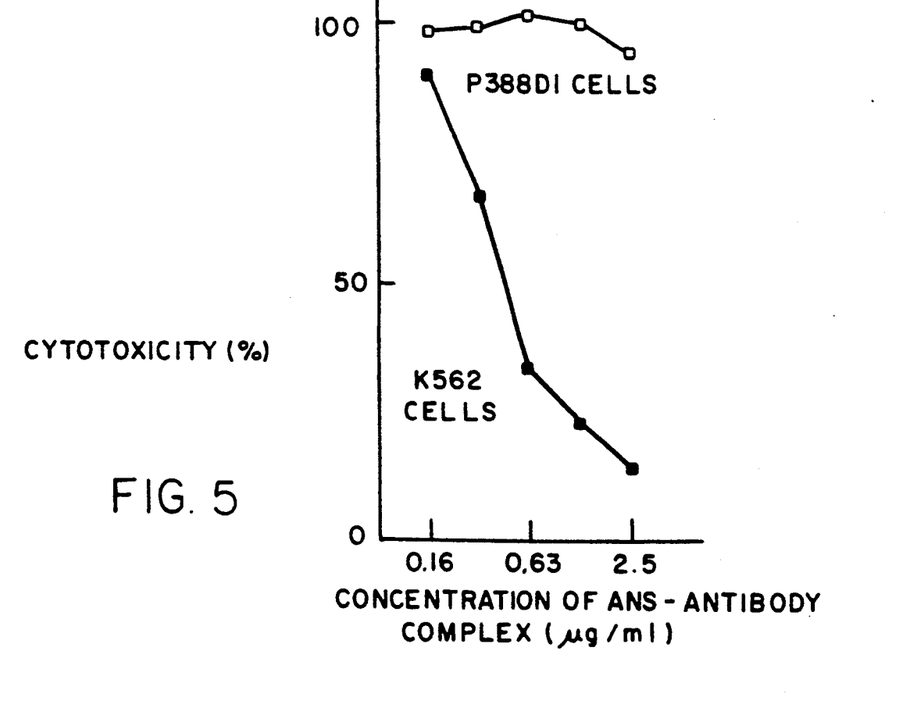
FIG. 5 shows the results of cytotoxicity test of anti-ANS-anti-hTfR bispecific antibody prepared in Example 3.
Figure 6:
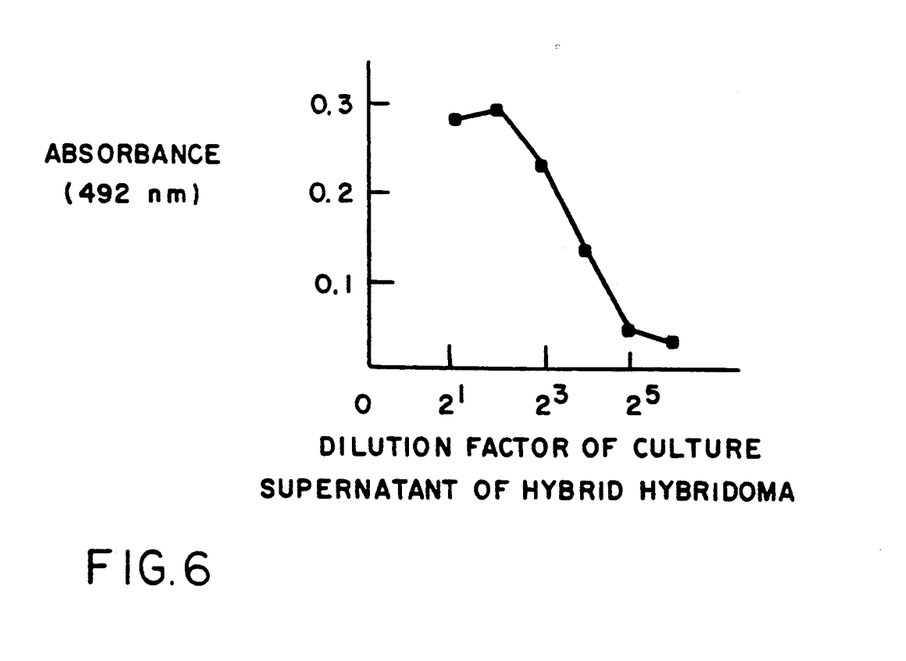
FIG. 6 shows the antibody dilution curve of the culture supernatant of RCAS1-488.

In FIG. 4, Peak 1 corresponded to the elution position of anti-ANS antibody AS6-44.9, and Peak 3 to the elution position of anti-hTfR antibody 22C6. The antibody elution fractions of respective peaks were assayed by the ELISA method for bispecific antibody assay described in Example 2-②. As a result, only Peak 2 showed strong antibody activity; it was demonstrated that the desired bispecific hybrid antibody ATF1-170 was eluted in Peak 2.

About 2.2 mg of the bispecific antibody was obtained from 5 ml of ascites fluid by the present method.

EXAMPLE 4

(Selective cytotoxicity of anti-ANS-anti-hTfR bispecific monoclonal antibody)

The purified anti-ANS-anti-hTfR bispecific antibody obtained in Example 3 was reacted with 5 molar equivalents of ansamitocin at 5° C. for 1 hour, and then the reaction mixture was subjected to a column of Sephadex G-25 equilibrated with PBS to collect a complex of ANS with the bispecific antibody.

The ANS-antibody complex solution (0.5 ml/well) was added to a plate to which human leukemia cells (K562: $1.0\times10^4$ cells/0.5 ml/well) or mouse leukemia cells ($P388D_1$; $1.0\times10^4$ cells/0.5 ml/well) were seeded and cultivation was conducted at 37° C. for 4 days. After the cultivation, the number of cells was determined by a Coulter counter and the cytotoxicity of the ANS-antibody complex was estimated. The results are shown in FIG. 5.

The ANS-antibody complex exhibited a potent cytotoxic effect against human leukemia cell line K562 which has hTfR and a strong binding activity with the bispecific antibody of the present invention, but little cytotoxic effect on mouse leukemia cell line $P388D_1$ which has no hTfR.

EXAMPLE 5

(Production of anti-ANS-anti-human renal cell carcinoma bispecific hybrid monoclonal antibody)

① Cell Fusion

According to the method of Example 2, the anti-ANS-antibody-producing hybridoma AS6-44.9, obtained in Example 1, and the anti-human renal cell carcinoma antibody-producing hybridoma RCS-1, obtained in Reference Example 4, were each incubated in an Iskove-Ham F12 mixed medium containing 0.5 μg/ml FITC for hybridoma AS6-44.9 or 1.5 μg/ml TRITC for hybridoma RCS-1 at 37° C. for 30 minutes for fluorescent staining. After addition of an LSM solution (commercially available from Wako Pure Chemical Industries, Ltd.) and removal of dead cells, these two hybridomas were mixed together at a ratio of 1:1 and subjected to cell fusion using PEG6000.

After incubation for 2 hours at 37° C., the cells were applied to FACS, whereby 25,000 fluorescein-rhodamine double stained cells were sorted. These double-stained cells (10 cells/well) were sown to and cultivated in a 96-well microplate seeded with $5\times10^5$ cells/well mouse thymocytes as feeder cells, with 10 double-stained cells per well.

② Selection and Cloning of Hybrid Hybridomas

The culture supernatants in the wells in which cell proliferation occurred 1 to 2 weeks after cell fusion were subjected to the following ELISA procedure for bispecific antibody assay to determine their antibody titer. To a microplate on which renal cancer AM-RC-7 cells ($10^4$ cells/well) were adsorbed the subject culture supernatant of hybrid hybridomas was added, followed by reaction at room temperature for 2 hours. After the plate was washed with a culture medium, an HRP-labeled (maytansinol 3-α-aminophenylacetate)-HSA was added, followed by reaction at room temperature for 2 hours. Then, the plate was washed. The activity of the enzyme bound to the solid phase was determined by the method described in Reference Example 1-②.

Wells showing a high level of hybrid antibody activity were subjected to cloning by limiting dilution method, whereby the desired bispecific-antibody-producing tetraoma RCAS1-488 was obtained. FIG. 6 shows the antibody dilution curve of the culture supernatant of RCAS1-488.

③ Purification of Hybrid Antibody $5\times10^6$ tetraoma cells per mouse were intraperitoneally inoculated to six BALB/c mice which had been intraperitoneally given 0.5 ml mineral oil. Ascites fluid retention began to occur 14 to 18 days later. The ascites fluid was collected and subjected to salting-out with 45 to 50% saturated ammonium sulfate to yield an IgG fraction. After dialysis against 20 mM PBS (pH 7.5), this fraction was applied to a column of Cellulofine coupled with PDM-3-$C_{20}$-ρ-aminobenzyl ether and eluted with 0.2M glycine-HCl buffer solution (pH 2.9). The acidically eluted fraction was dialyzed against PBS and then subjected to high performance liquid chromatography using a column of hydroxyapatite to yield the anti-ANS-anti-human renal cell carcinoma bispecific hybrid antibody of the present invention.

About 5.8 mg of the bispecific antibody was obtained from 20 ml of ascites fluid.

What is claimed is:

1. A hybrid monoclonal antibody having binding affinities to a cytotoxic ansamitocin derivative and to a target antigen, wherein the cytotoxicity of the ansamitocin derivative is reduced when bound to the antibody.

2. A hybrid monoclonal antibody according to claim 1, wherein the target antigen is a tumor-associated antigen.

3. A hybrid monoclonal antibody according to claim 2, wherein the tumor-associated antigen is human transferrin receptor.

4. A hybrid monoclonal antibody according to claim 2, wherein the tumor-associated antigen is human renal cell carcinoma-associated glycoprotein.

5. A hybrid monoclonal antibody according to claim 1, wherein the ansamitocin derivative is a compound of the formula:

wherein R represents a hydrogen atom or an acyl group derived from a carboxylic acid; Q represents a hydroxyl group or a mercapto group; X represents a chlorine atom or a hydrogen atom; Y represents a hydrogen atom, a lower alkylsulfonyl group, an alkyl group or an aralkyl group, said alkyl and aralkyl groups being unsubstituted or substituted, or a 4,5-deoxy derivative thereof.

6. A hybrid monoclonal antibody according to claim 5, wherein R represents a group of the formula:

wherein $R^1$ represents an alkyl group having 1 to 18 carbon atoms, or a group of the formula:

wherein $R^2$, $R^3$ and $R^4$ represent an alkyl group having 1 to 18 carbon atoms; Q represents a hydroxyl group or a mercapto group; X represents a chlorine atom; Y represents an alkyl group having 1 to 8 carbon atoms.

7. An immunocomplex comprising a cytotoxic ansamitocin derivative with a hybrid monoclonal antibody, said hybrid monoclonal antibody having binding affinities both to a cytotoxic ansamitocin derivative and to a target antigen, wherein the cytotoxicity of the ansamitocin derivative is reduced when bound to the antibody.

8. An immunocomplex according to claim 7, wherein the target antigen is a tumor-associated antigen.

9. An immunocomplex according to claim 8, wherein the tumor-associated antigen is human transferrin receptor.

10. An immunocomplex according to claim 8, wherein the tumor-associated antigen is human renal cell carcinoma-associated glycoprotein.

11. An immunocomplex according to claim 7, wherein the ansamitocin derivative is a compound of the formula:

wherein R represents a hydrogen atom or an acyl group derived from a carboxylic acid; Q represents a hydroxyl group or a mercapto group; X represents a chlorine atom or a hydrogen atom; Y represents a hydrogen atom, a lower alkylsulfonyl group, an alkyl group or an aralkyl group, said alkyl and aralkyl groups being unsubstituted or substituted, or a 4,5-deoxy derivative thereof.

12. An immunocomplex according to claim 11, wherein R represents a group of the formula:

wherein $R^1$ represents an alkyl group having 1 to 18 carbon atoms, or a group of the formula:

wherein $R^2$, $R^3$ and $R^4$ represent an alkyl group having 1 to 18 carbon atoms; Q represents a hydroxyl group or a mercapto group; X represents a chlorine atom; Y represents an alkyl group having 1 to 8 carbon atoms.

13. An immunocomplex according to claim 7, wherein the ansamitocin derivative is ansamitocin.

14. A polydoma which has an ability to produce a hybrid monoclonal antibody having binding affinities both to a cytotoxic ansamitocin derivative and to a target antigen, wherein the cytotoxicity of the ansamitocin derivative is reduced when bound to the antibody.

15. A polydoma according to claim 14, which is a tetraoma.

16. A polydoma according to claim 14, wherein the target antigen is a tumor-associated antigen.

17. A polydoma according to claim 16, wherein the tumor-associated antigen is human transferrin receptor.

18. A polydoma according to claim 16, wherein the tumor-associated antigen is human renal cell carcinoma-associated glycoprotein.

19. A polydoma according to claim 14, wherein the ansamitocin derivative is a compound of the formula:

wherein R represents a hydrogen atom or an acyl group derived from a carboxylic acid; Q represents a hydroxyl group or a mercapto group; X represents a chlorine atom or a hydrogen atom; Y represents a hydrogen atom, a lower alkylsulfonyl group, an alkyl group or an aralkyl group, said alkyl and aralkyl groups being unsubstituted or substituted, or a 4,5-deoxy derivative thereof.

20. A polydoma according to claim 19, wherein R represents a group of the formula:

wherein R¹ represents an alkyl group having 1 to 18 carbon atoms, or a group of the formula:

$$-COCH-N\begin{matrix}R^2\\|\\\end{matrix}\begin{matrix}R^3\\/\\ \backslash\\COR^4\end{matrix}$$

wherein R², R³ and R⁴ represent an alkyl group having 1 to 18 carbon atoms; Q represents a hydroxyl group or a mercapto group; X represents a chlorine atom; Y represents an alkyl group having 1 to 8 carbon atoms.

21. A process for producing a hybrid monoclonal antibody having binding affinities both to a cytotoxic ansamitocin derivative and to a target antigen, wherein the cytotoxicity of the ansamitocin derivative is reduced when bound to the antibody, which comprises cultivating a polydoma which has an ability to produce said hybrid monoclonal antibody and recovering said hybrid monoclonal antibody from the culture.

22. A process for producing an immunocomplex comprising a cytotoxic ansamitocin derivative with a hybrid monoclonal antibody, said hybrid monoclonal antibody having binding affinities both to a cytotoxic ansamitocin derivative and to a target antigen, wherein the cytotoxicity of the ansamitocin derivative is reduced when bound to the antibody, which comprises reacting said ansamitocin derivative with said hybrid monoclonal antibody.

23. A process for producing a polydoma which has an ability to produce a hybrid monoclonal antibody having binding affinities to both to a cytotoxic ansamitocin derivative and to a target antigen, wherein the cytotoxicity of the ansamitocin derivative is reduced when bound to the antibody, which comprises fusing an animal cell which has an ability to produce an antibody to a cytotoxic ansamitocin derivative with an animal cell which has an ability to produce an antibody to a target antigen.

24. A process according to claim 23, wherein both of said animal cells are hybridoma.

* * * * *